United States Patent [19]

Young et al.

[11] Patent Number: 4,770,759
[45] Date of Patent: Sep. 13, 1988

[54] LITHIUM ION-SELECTIVE MEMBRANE ELECTRODE

[75] Inventors: Chung C. Young, Weston; John Hiti, Danvers, both of Mass.

[73] Assignee: Nova Biomedical Corporation, Waltham, Mass.

[21] Appl. No.: 883,108

[22] Filed: Jul. 8, 1986

[51] Int. Cl.$^4$ ............................................. G01N 27/46
[52] U.S. Cl. ..................... 204/418; 204/1 T
[58] Field of Search ................ 204/1 A, 416–419

[56] References Cited

U.S. PATENT DOCUMENTS

| | | | |
|---|---|---|---|
| 4,314,895 | 2/1982 | Spaziani et al. | 204/417 |
| 4,361,473 | 11/1982 | Young et al. | 204/418 |
| 4,504,368 | 3/1985 | Delton et al. | 204/418 |
| 4,523,994 | 6/1985 | Shono et al. | 210/500.28 |
| 4,554,362 | 11/1985 | Shono et al. | 549/352 |

OTHER PUBLICATIONS

Kitazawa et al., 106 J. Am. Chem. Soc. 6978 (1984).
Metzger et al., submitted to Anal. Chem. on Jun. 27, 1985.

*Primary Examiner*—T. Tung

[57] ABSTRACT

An electrode for determining the lithium content of a liquid sample to be tested, has a membrane containing a lithium ion selective compound and a plasticizer, the improvement wherein the plasticizer is a liquid, lipophilic dialkyl phthalate compound or a liquid phenyl phenyl ether compound that has a strong electron withdrawing group at an ortho position on one of the phenyl rings. The ion selective compound has the formula:

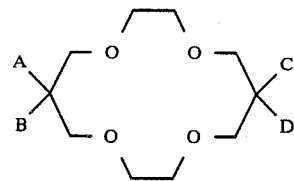

wherein A is an alkyl group having between 8 and 16 carbon atoms, B is an alkyl group having between 1 and 4 carbon atoms, and each C and D is, independently, a hydrogen atom or an alkyl group having between 1 and 16 carbon atoms, provided that both C and D are not alkyl groups having greater than 4 carbon atoms.

19 Claims, 1 Drawing Sheet

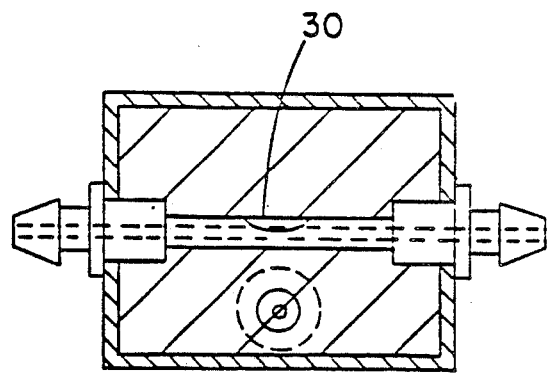

LITHIUM ION-SELECTIVE MEMBRANE ELECTRODE

BACKGROUND OF THE INVENTION

This invention relates to electrodes for determining the lithium ion content of a liquid sample.

Kitazawa et al., 106 J. Am. Chem. Soc. 6978 (1984) describe a membrane electrode composed of polyvinylchloride (PCV), o-nitrophenyl octyl ether, potassium tetrakis(4-chlorophenyl)borate (KTpClPB), and the lithium selective compound 3-dodecyl-3-methyl-1,5,8,12-tetraoxacyclotetradecane (3-dodecyl-3-methyl-14-Crown-4), which has the following formula:

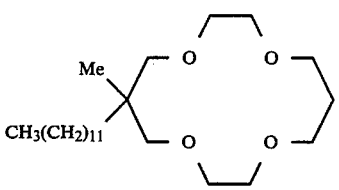

(1)

SUMMARY OF THE INVENTION

In general the invention features an improvement in an electrode for determining the lithium ion content of a liquid sample to be tested. The electrode has a membrane containing a plasticizer and a lithium selective compound of the formula:

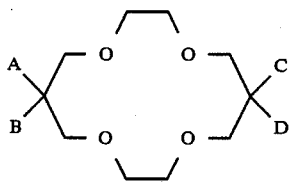

wherein A is an alkyl group having between 8 and 16 carbon atoms, B is an alkyl group having between 1 and 4 carbon atoms, and each C and D is, independently, a hydrogen atom or an alkyl group having between 1 and 16 carbon atoms, provided that both C and D are not alkyl groups having greater than 4 carbon atoms. The improvement is using as the plasticizer either a liquid, dialkyl phthalate compound, or a liquid phenyl phenyl ether compound that has at the ortho position (with respect to the ether linkage) of one of its phenyl rings a strong electron-withdrawing group.

In preferred embodiments, the dialkyl phthalate compound is of the formula:

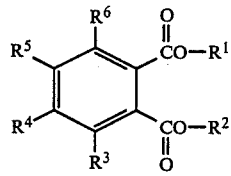

(2)

wherein each $R^1$ and $R^2$ is, independently, an alkyl group having between 4 and 18 carbon atoms; and each $R^3$, $R^4$, $R^5$, and $R^6$ is, independently, a hydrogen atom or an alkyl group having 8 or fewer carbons.

In other preferred embodiments, the phenyl phenyl ether compound is of the formula:

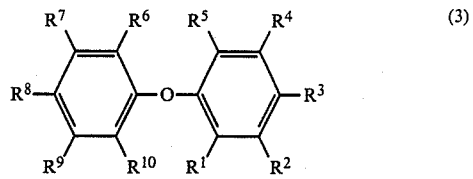

(3)

wherein $R^1$ is a nitro group, $R^2$, $R^3$, $R^4$, and $R^5$ are hydrogen atoms, and each $R^6$, $R^7$, $R^8$, $R^9$, and $R^{10}$ is, independently, either a hydrogen atom or an alkyl group comprising 7 or fewer carbon atoms.

In other preferred embodiments the membrane further is composed of a plastic material and an anion excluder.

The electrode containing the membrane of the invention provides accurate measurements of lithium ion content of liquids, particularly serum. Moreover, the membrane's drift stability is excellent, so that drift-related measurement errors are minimized.

Other objects, features, and advantages of this invention will be apparent to those skilled in the art from the following detailed description of the preferred embodiment thereof, and from the claims.

DESCRIPTION OF THE PREFERRED EMBODIMENT

The FIGURE is a sectional view of an electrode assembly embodying the invention.

The electrode assembly shown in the FIGURE is as shown and described in Spaziani et al., U.S. Pat. No. 4,233,136, hereby incorporated by reference.

In the preferred embodiment of the present invention, membrane 30 is composed of an organic plastic matrix, PVC, which contains 3-dodecyl-3-methyl-14-Crown-4, the plasticizer di(2-ethyl-hexyl)phthalate (dioctyl phthalate; DOP), and KTpClPB, an anion excluder. The membrane materials are all soluble in the volatile solvent tetrahydrofuran.

The amount of PVC, which provides support for the membrane, is controlled to provide support without interfering with the electrochemical properties of the membrane. The membrane comprises 20 to 45% (preferably 25 to 30%) PVC by weight. If less than 20% PVC by weight is used, the membrane generally is not strong enough. If greater than 55% PVC by weight is used, the performance of the membrane begins to degrade.

The lithium ion selective compound 3-dodecyl-3-methyl-14-Crown-4 serves as the $Li^+$ carrier in the membrane. The membrane comprises 1 to 10% (preferably 1 to 2%) carrier by weight. If less than 1% carrier by weight is used, the selectivity of the electrode diminishes. If greater than 10% carrier by weight is used, the carrier may become insoluble in the plasticizer, causing the electrode's performance to degrade.

The plasticizer, DOP (available from Aldrich Chem. Co., catalog no. D20, 115-4), serves as the solvent for the lithium carrier in the membrane. The membrane comprises 50 to 80% (preferably 65–75%) DOP by weight. If less than 50% by weight DOP is used, the lithium carrier may crystallize in the membrane. If greater than 80% by weight DOP is used, the membrane may be weak.

The anion excluder, KTpClPB (available from Fluka Chem. Corp.) helps prevent binding of small anions to the membrane. The membrane comprises 0.5 to 2% (preferably 0.7%) KTpClPB by weight. If less than 0.5% by weight KTpClPB is used, the efficiency of small anion exclusion diminishes. If greater than 2% by weight KTpClPB is used, the selectivity of the electrode is adversely effected.

To make the membrane, 350 mg of high molecular weight PVC polymer in powder form (available from Aldrich Chem. Co. catalog no. 18956-1) is dissolved in 5 ml of tetrahydrofuran. To this solution are then added 834 mg of non-volatile solvent plasticizer DOP, together with 17.5 mg 3-dodecyl-3-methyl-14-Crown-4 and 8.8 mg KTpClPB.

The membrane is made from the solution thus formed, as described in Spaziani et al. Such a membrane demonstrated good mechanical strength and good analytical performance, as shown in line 1 of the Table. The slope was near Nernstian, 56.8 mV, and drift in both serum and aqueous solution was very slight.

The drifts for the membranes listed in the Table are determined on the basis of the related concepts of drift and calibration.

the electrode in the sample (either an aqueous solution or serum) with the linear calibration graph.

The concept of drift comes in when the electrode potential is again measured, after an analysis, against one the standards (in this case standard A) The difference between the potential of the standard A before and after the analysis is drift; the larger the absolute value of this number, the poorer the performance of the electrode in this respect, and the more significant the resultant measurement errors. As shown in the Table 1, the preferred electrode (line 1) has low drift when used in a serum sample after previously having been used in an aqueous sample, and when used in an aqueous sample after previously having been used in a serum sample.

3-Dodecyl-3-methyl-14-Crown-4

The first step in the preparation of 3-dodecyl-3-methyl-14-Crown-4 is to prepare 3,7-dioxanonane-1,9-diol ditosylate, according to the general procedure of Dale et al., 26 Acta. Chem. Scand. 1471 (1972).

To 280 ml (5.0 mol) of ethylene glycol is added 17.25 g (0.75 mol) of sodium metal in small pieces, in order to control the exothermic reaction. The reaction mixture is cooled to room temperature and 80.89 g (0.393 mol) of

TABLE

| Membrane | Ion Selective Compound | Plasticizer | Ion Selective Compound % (by weight) | Plasticizer % (by weight) | PVC % (by weight) | KTpClPB % (by weight) | Slope (mV) | Standard A Drift Range (mV) | |
|---|---|---|---|---|---|---|---|---|---|
| | | | | | | | | Serum-aqueous | Aqueous-Serum |
| 1 | 3-dodecyl-3-methyl-14-Crown-4 | DOP | 1.4 | 69.9 | 28.0 | 0.7 | 56.8 | 0–0.6 | 0–0.5 |
| 2 | 3-dodecyl-3-methyl-14-Crown-4 | DOP | 2.8 | 68.9 | 27.5 | 0.7 | 56.2 | 0–0.8 | 0–0.6 |
| 3 | 3-dodecyl-3-ethyl-14-Crown-4 | DOP | 1.4 | 69.9 | 28.0 | 0.7 | 53.0 | 0.0–0.2 | 0.1–0.4 |
| 4 | 3-dodecyl-3-methyl-14-Crown-4 | NPPE[A] | 1.4 | 69.9 | 28.0 | 0.4 | 54.1 | 0.0–0.8 | 0.0–1.0 |
| 5 | 3-dodecyl-3-ethyl-14-Crown-4 | NPHPE[B] | 1.4 | 69.9 | 28.0 | 0.7 | 57.1 | 0.0–0.3 | 0.4–0.5 |
| 6 | 3-dodecyl-3-methyl-14-Crown-4 | DOP | 2.8 | 69.0 | 27.6 | 0.7 | 56.8 | 0.0–0.3 | 0.0–0.6 |
| 7 | 3-dodecyl-3-methyl-14-Crown-4 | DiNP[C] | 2.8 | 69.0 | 27.6 | 0.7 | 53.3 | 0.0–0.7 | 0.0–0.7 |
| 8 | 3-dodecyl-3-methyl-14-Crown-4 | NPPE[A] | 2.8 | 69.0 | 27.6 | 0.7 | 54.1 | 0.0–0.8 | 0.0–1.0 |
| 9 | 3-dodecyl-3-methyl-14-Crown-4 | NPHPE[B] | 2.8 | 69.0 | 27.6 | 0.7 | 54.4 | 0.1–0.4 | 0.0–0.8 |
| 10 | 3-dodecyl-3-ethyl-14-Crown-4 | DOP | 2.8 | 69.0 | 27.6 | 0.7 | 53.0 | 0.0–0.2 | 0.1–0.4 |
| 11 | 3-dodecyl-3-ethyl-14-Crown-4 | NPHPE[B] | 2.8 | 69.0 | 27.6 | 0.7 | 57.1 | 0.0–0.3 | 0.4–0.5 |

[A] 2-nitrophenyl phenyl ether
[B] 2-nitrophenyl 4-hexylphenyl ether
[C] diisononyl phthalate In ion specific electrode measurements the electrodes must be calibrated prior to their use in an analysis. In all cases, at least a two point calibration is performed; in this instance, two internal standards were used. One standard, B, contains 10 mM $Li^+$ and 50 mM $Na^+$, while a second, A, contains 1 mM $Li^+$ and 140 mM $Na^+$. (Employing calibration solutions which have a background of potentially interfering $Na^+$ ensures that the electrode possesses selectivity of $Li^+$ over $Na^+$.) Prior to an analysis, the lithium electrode is calibrated with the two standards. With each standard, the electrode developes an electrical potential proportional to the logarithm of the concentration of $Li^+$. According to the Nernst equation, the logarithm of concentration and potential are linearly related: the difference in potential for a ten fold change in concentration should be 59.1 mv at 25° C. Measurement of $Li^+$ in an unknown is performed by comparing the potential developed by 1,3-dibromopropane (available from Aldrich Chem. Co., catalog no. 12,590-3) is added dropwise. The reaction is heated to 100° C. for 6 hours. Excess ethylene glycol then is removed by simple distillation under aspirator pressure and 3,7-dioxanonane-1,9-diol is obtained in 17.9% yield from the reaction mixture by fractional distillation at 108°–112° C. and 0.025 mm Hg. A solution of 11.47 g (0.072 mol) of the diol and 17.4 ml (0.215 mole) pyridine in 100 ml of methylene chloride is added to a stirred solution of 26.68 g of tosyl chloride (0.15 mol) in 140 ml methylene chloride. Following addition, the reaction is allowed to stand stirred at 0° C. for 24 hours. The mixture then is washed with water, 10% HCl, and once again with water. The mixture is dried over anhydrous sodium sulfate, and the solvent is removed under reduced pressure to give 33.51 g of a clear oil. Kugelrohr distillation (80° C., 0.005 mm Hg) removes unreacted tosyl chloride, leaving 29.43 g of 3,7-dioxanonane-1,9-diol ditosylate as a slightly brown oil.

The second step in the preparation of 3-dodecyl-3-methyl-14-Crown-4 is to prepare 2-dodecyl-2-methylpropane-1,3-diol.

A solution of 48.72 g (0.277 mol) of diethyl methylmalonate (available from Aldrich Chem. Co., Catalog No. 12,613-6) in 60 ml of $N_1N$-dimethyl formamide (DMF) is added dropwise to a stirred solution of 6.86 g (0.277 mol) of sodium hydride (NaH) in DMF. The reaction mixture is heated during the dropwise addition of a solution of 72.17 g (0.284 mol) of 1-bromododecane (Aldrich Chem. Co., catalog no. B6,555-1) in 60 ml DMF. The reaction is heated to 80° C. and stirred overnight, after which the NaBr that precipitated is filtered and the DMF removed in vacuo. The oily residue obtained is dissolved in ether and filtered again to remove all NaBr. The ether solution is washed with water followed by saturated NaCl. The solution is dried over anhydrous sodium sulfate and the ether is removed under reduced pressure to yield a clear, yellow oil. Fractional distillation (130°–138° C., 0.007 mm Hg) gives 82.28 g (88% overall yield) of diethyl dodecylmethylmalonate as a clear oil. The oil is dissolved in 175 ml of anhydrous ether, and the solution is added dropwise to a suspension of 19.21 g (0.480 mol) of lithium aluminum hydride. The reaction is stirred overnight, carefully quenched, and filtered. The solvent is removed in vacuo and the solid obtained is recrystallized and dried to give 51.00 g (81% overall yield) of 2-dodecyl-2-methylpropane-1,3-diol as a white solid (mp 67°–68° C.).

The final step in the preparation of 3-dodecyl-3-methyl-14-Crown-4 is the cyclization of 2-dodecyl-2-methylpropane-1,3-diol with 3,7-dioxanone-1,9-diol ditosylate, according to the general procedure described in Kitazawa et al.

A solution of 2.74 g (10.6 mmol) of 2-dodecyl-2-methylpropane-1,3-diol in 40 ml of p-dioxane is added dropwise to a stirred suspension of 0.63 g (25.5 mmol) of NaH in dioxane. A solution of 5.01 g (10.6 mmol) 3,7-dioxanonane-1,9-diol ditosylate in 50 ml of dioxane is added and the reaction is refluxed overnight. The reaction mixture is filtered to remove the precipitated sodium tosylate, and the dioxane is evaporated under reduced pressure. The oily residue obtained is dissolved in methylene chloride and washed with water and saturated potassium chloride solution. After drying over anhydrous magnesium sulfate, the solvent is evaporated in vacuo to give a colored oil. Column chromatography of this material followed by distillation (135°–145° C., 0.005 mm Hg) yields 0.940 g (23% overall yield) of 3-dodecyl-3-methyl-14-Crown-4 as a clear oil, which crystallized upon standing at 10° C.

OTHER EMBODIMENTS

Other embodiments are within the following claims. For example, the lithium ion selective compound can be of any configuration within general formula (4).

In formula (4), A can be an alkyl group having between 8 and 16 carbons. If A is an alkyl group having less than 8 carbons, the lithium ion specific compound may not be lipophilic enough; if A is an alkyl group having more than 16 carbons, the compound may not be soluble enough in the plasticizer. B can be an alkyl group having 1 to 4 carbons. Having an alkyl group at B increases $Li^+$ specificity of the compound; if the alkyl group has more than 4 carbons, however, the $Li^+$ specificity may decline.

In formula (4), it is preferred that C and D be hydrogen. C and D, however, can be alkyl groups having between 1 and 16 carbons, provided that C and D both are not alkyl groups having more than 4 carbons.

Where C and D in formula (4) are hydrogen atoms, ion selective compounds in which A and B vary from the preferred compound can be prepared from the corresponding starting materials. Accordingly, to vary the length of A, the appropriate diethyl malonate compound should be used in place of diethyl methylmalonate in the synthesis described above; for example in the synthesis of 3-dodecyl-3-ethyl-14-Crown-4, diethyl ethylmalonate (available from Aldrich Chem. Co., catalog No. D9,520-4) is used in the reaction with 1-bromododecane. Similarly, to vary the length of B, the appropriate 1-bromoalkane should be used in place of 1-bromododecane.

Where C and D are not hydrogen atoms, the appropriate 2-substituted 1,3-dibromopropane should be used in place of 1,3-dibromopropane in the above described synthesis.

A number of dialkyl phthalate compounds can be used as the plasticizer, so long as the compound is both a liquid at 25° C. (so that the other membrane components such as the lithium ion selective compound can dissolve in it) and lipophilic (to ensure that the plasticizer does not leach significantly into the aqueous samples). These properties generally are present where in general formula (2) $R^1$ and $R^2$ are, independently, alkyl groups having between 4 and 18 carbons. If $R^1$ and/or $R^2$ are alkyl groups having more than 18 carbons, the plasticizer may be a solid. If $R^1$ and/or $R^2$ are alkyl groups having less than 4 carbons, the plasticizer may not be lipophilic enough. Plasticizers in which $R^1$ and $R^2$ are the same may be synthesized by esterifying phthalic acid with the appropriate alcohol.

$R^3$, $R^4$, $R^5$, and $R^6$ in formula (2) can be, in addition to H, short chain alkyl groups (those with 7 or less carbon atoms). The total number of carbon atoms in $R^3$, $R^4$, $R^5$, and $R^6$ in general should not exceed 8; above 8 carbon atoms, the plasticizer may exist as a solid.

In other embodiments the plasticizer is a phenyl phenyl ether compound having general formula (3) in which at the ortho position ($R^1$) of one ring is a functional group, such as nitro, chloro, cyano, or trifluoromethyl, that has a strong electron-withdrawing ability. $R^1$ preferably is a nitro group. $R^2$ through $R^{10}$ can be any functional group, so long as the group either does not detract substantially from the lipophilic character of the plasticizer, or increase the molecular weight of the plasticizer to such an extent that the plasticizer is a solid at 25° C. Preferably $R^2$–$R^5$ are hydrogen atoms, and $R^6$–$R^{10}$ are either hydrogen atoms or alkyl groups that, in total, contain 7 or less carbon atoms (if $R^6$–$R^{10}$ total more than 7 carbon atoms, the resulting plasticizer may be a solid.) Most preferably, $R^2$–$R^9$ are hydrogen atoms, and $R^8$ is either a hydrogen atom or an alkyl group having between 1 and 7 carbon atoms.

The plasticizer 2-nitrophenyl 4-hexylphenyl ether (NPHPE) is synthesized by reacting p-hexylphenol (available from Kodak Lab. Chem., catalog No. 14,319) with 2-chloronitrobenzene (available from Aldrich Chem. Co., catalog No. C5,910-6). 1.44 g (0.06 mol) of sodium hydride is suspended in 75 ml of THF under $N_2$. 9.01 g (0.05 mol) of p-hexylphenol are dissolved in 25 ml of THF and added dropwise to the suspension. 7.86

(0.05 mol) of 2-chloronitrobenzene are dissolved in 25 ml of THF and added dropwise to the reaction mixture; the resultant mixture is refluxed for 88 hours. Following reflux 3 ml of acetic acid are added, and the reaction is filtered through filter cel, concentrated, chromatographed twice on silical gel, and Kugelrohr distilled at 0.01 mm Hg, 140°-150° C., to yield 4.7 g (34% yield) of 2-nitrophenl 4-hexylphenyl ether as an orange oil.

Other phenyl-phenyl ethers are similarly prepared. For example, 2-nitropheyl 4-butylphenyl ether is prepared by reacting p-butylphenol (available from Kodak Lab. Chem., catalog No. 14,062) with 2-chloronitrobenzene.

Other anion excluders such as tetraphenyl borate and picric acid can be used in place of KTpClPB. Moreover, although it is preferred that the membrane contain an anion excluder, a functional membrane is obtained even if an excluder is not present.

The Table presents the analytical results obtained with other membranes of the invention. All of the listed electrodes gave good analytical results.

We claim:

1. In an electrode for determining the lithium content of a liquid sample to be tested, said electrode comprising a plasticizer and a membrane comprising a lithium ion selective compound having the formula

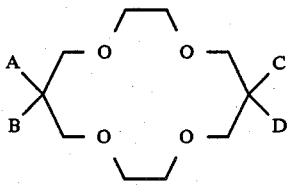

wherein A is an alkyl group comprising between 8 and 16 carbon atoms, B is an alkyl group comprising between 1 and 4 carbon atoms, and each C and D is, independently, a hydrogen atom or an alkyl group comprising between 1 and 16 carbon atoms, provided that both C and D are not alkyl groups comprising greater than 4 carbon atoms, the improvement wherein said plasticizer is a liquid dialkyl phthalate compound.

2. The electrode of claim 1 wherein said dialkyl phthalate compound is of the formula:

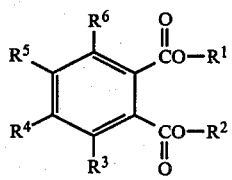

wherein each $R^1$ and $R^2$ is, independently, an alkyl group comprising between 4 and 18 carbon atoms; and each $R^3$, $R^4$, $R^5$, and $R^6$ is, independently, a hydrogen atom or an alkyl group comprising 8 or fewer carbons.

3. The electrode of claim 2 wherein each $R^1$ and $R^2$ is, independently, an alkyl group comprising either 8 or 9 carbon atoms.

4. The electrode of claim 2 or 3 wherein $R^3$, $R^4$, $R^5$, and $R^6$ are hydrogen atoms.

5. The electrode of claim 1 wherein said plasticizer is di(2-ethyl-hexyl)phthalate.

6. In an electrode for determining the lithium content of a liquid sample to be tested, said electrode comprising a plasticizer and a membrane comprising a lithium ion selective compound having the formula

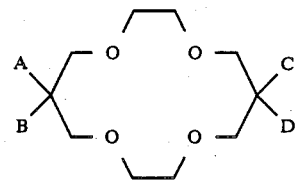

wherein A is an alkyl group comprising between 8 and 16 carbon atoms, B is an alkyl group comprising between 1 and 4 carbon atoms, and each C and D is, independently, a hydrogen atom or an alkyl group comprising between 1 and 16 carbon atoms, provided that both C and D are not alkyl groups comprising greater than 4 carbon atoms, the improvement wherein said plasticizer is a liquid phenyl phenyl ether compound comprising at the ortho position of one phenyl ring a strong electron-withdrawing group.

7. The electrode of claim 6 wherein said compound is of the formula:

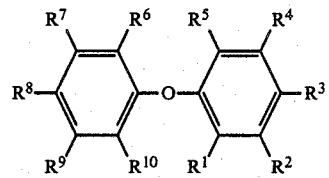

wherein $R^1$ is a nitro group and each $R^2$, $R^3$, $R^4$, $R^5$, $R^6$, $R^7$, $R^8$, $R^9$, and $R^{10}$ is, independently, any functional group that does not increase the molecular weight of said compound to such an extent that said compound is a solid at 25° C.

8. The electrode of claim 7 wherein $R^2$, $R^3$, $R^4$, and $R^5$ are hydrogen atoms, and each $R^6$, $R^7$, $R^8$, $R^9$, and $R^{10}$ is, independently, either a hydrogen atom or an alkyl group comprising 7 or fewer carbon atoms.

9. The electrode of claim 7 or 8 wherein $R^6$, $R^7$, $R^9$, and $R^{10}$ are hydrogen atoms.

10. The electrode of claim 6 wherein said plasticizer is 2-nitrophenyl 4-hexylphenyl ether.

11. The electrode of claim 1 or 6 wherein C and D are hydrogen atoms.

12. The electrode of claim 1, 6 or 11 wherein B is an alkyl group comprising either 1 or 2 carbon atoms.

13. The electrode of claim 1, 6 or 11 wherein A is an alkyl group comprising 12 carbon atoms.

14. The electrode of claim 1 or 6 wherein said lithium ion selective compound is 3-dodecyl-3-methyl-1,5,8,12-tetraoxacyclotetradecane.

15. The electrode of claim 1 or 6 wherein said membrane further comprises a plastic material.

16. The electrode of claim 15 wherein said plastic material is polyvinylchloride.

17. The electrode of claim 15 wherein said membrane further comprises an anion excluder.

18. The electrode of claim 17 wherein said anion excluder is potassium tetrakis(4-chlorophenyl)borate.

19. The electrode of claim 17 wherein said plasticizer comprises 50 to 80% of said membrane, by weight; said plastic material comprises 20 to 45% of said membrane, by weight; said ion selective compound comprises 1 to 10% of said membrane, by weight; and said anion excluder comprises 0.5 to 2% of said membrane, by weight.

* * * * *